(12) United States Patent
Erhard et al.

(10) Patent No.: US 9,529,508 B2
(45) Date of Patent: Dec. 27, 2016

(54) MEDICAL IMAGE SYSTEM

(75) Inventors: Klaus Erhard, Hamburg (DE); Michael Grass, Buchholz in der Nordheide (DE)

(73) Assignee: Koninklijke Philips N.V., Eindhoven (NL)

( * ) Notice: Subject to any disclaimer, the term of this patent is extended or adjusted under 35 U.S.C. 154(b) by 383 days.

(21) Appl. No.: 13/879,769

(22) PCT Filed: Oct. 13, 2011

(86) PCT No.: PCT/IB2011/054528
§ 371 (c)(1),
(2), (4) Date: Apr. 16, 2013

(87) PCT Pub. No.: WO2012/052887
PCT Pub. Date: Apr. 26, 2012

(65) Prior Publication Data
US 2013/0205247 A1 Aug. 8, 2013

(30) Foreign Application Priority Data
Oct. 19, 2010 (EP) .................................... 10188035

(51) Int. Cl.
*G06F 3/0481* (2013.01)
*G06F 3/0484* (2013.01)
(Continued)

(52) U.S. Cl.
CPC ........... *G06F 3/04842* (2013.01); *G06F 3/016* (2013.01); *G06F 19/321* (2013.01); *G06T 7/0012* (2013.01);
(Continued)

(58) Field of Classification Search
CPC ............................... G06F 3/016; G06F 3/0481
See application file for complete search history.

(56) References Cited

U.S. PATENT DOCUMENTS 6,128,006 A 10/2000 Rosenberg
6,628,815 B2 * 9/2003 Wang ............................ 382/132
(Continued)

FOREIGN PATENT DOCUMENTS

EP 1587026 A1 10/2005
JP H08166995 A 6/1996
(Continued)

OTHER PUBLICATIONS

Olivier Bau et al TeslaTouch, Proceedings of the 23nd Annual ACM Symposium on User Interface Software and Technology, Oct. 2010, pp. 283-292.

*Primary Examiner* — Phenuel Salomon

(57) ABSTRACT

A system for alerting a user to a region of interest within an image of interest, the image of interest being one of a sequence of medical images from a patient, the system sequentially displaying the sequence of medical images for enabling the user to navigate through the sequence of medical images. The system includes an input for receiving a sequence navigation command from the user for requesting the system to display images from the sequence of medical images as part of pixel data shown on a display, and a signal generator for providing a sensory signal to the user in separation from the pixel data and in dependence on a difference between a position of a currently displayed image of the sequence of medical images in the sequence and a position of the image of interest in the sequence.

20 Claims, 3 Drawing Sheets

(51) Int. Cl.
*G06F 3/01* (2006.01)
*G06F 19/00* (2011.01)
*G06T 7/00* (2006.01)

(52) U.S. Cl.
CPC ......... *G06F 19/345* (2013.01); *G06T 2200/24* (2013.01); *G06T 2207/10081* (2013.01); *G06T 2207/10112* (2013.01); *G06T 2207/30068* (2013.01)

(56) References Cited

U.S. PATENT DOCUMENTS

| | | | |
|---|---|---|---|
| 6,630,937 B2* | 10/2003 | Kallergi et al. | 345/619 |
| 6,813,394 B1* | 11/2004 | Matsumoto et al. | 382/305 |
| 6,891,920 B1* | 5/2005 | Minyard | A61B 6/469 378/37 |
| 6,909,795 B2* | 6/2005 | Tecotzky | G06F 19/321 382/128 |
| 7,174,515 B1 | 2/2007 | Marshall | |
| 7,212,661 B2* | 5/2007 | Samara | G06F 17/30247 382/131 |
| 7,630,533 B2* | 12/2009 | Ruth et al. | 382/131 |
| 8,314,777 B2 | 11/2012 | Ikeda et al. | |
| 8,830,307 B2 | 9/2014 | Hirakawa | |
| 2003/0063198 A1* | 4/2003 | Yokokawa | 348/231.2 |
| 2005/0034084 A1* | 2/2005 | Ohtsuki et al. | 715/864 |
| 2005/0285853 A1* | 12/2005 | Morita et al. | 345/419 |
| 2008/0155468 A1 | 6/2008 | Rosander | |
| 2008/0317386 A1* | 12/2008 | Wood et al. | 382/307 |
| 2009/0002328 A1* | 1/2009 | Ullrich | G06F 3/016 345/173 |
| 2009/0087067 A1* | 4/2009 | Khorasani | 382/132 |
| 2010/0023857 A1 | 1/2010 | Mahesh | |
| 2010/0086188 A1 | 4/2010 | Ruth | |
| 2011/0261021 A1* | 10/2011 | Modarres | G06F 3/016 345/177 |

FOREIGN PATENT DOCUMENTS

| | | |
|---|---|---|
| JP | 08166995 A | 7/2003 |
| JP | 2004173910 A | 6/2004 |
| JP | 06128006 A | 5/2006 |
| JP | 08166995 A | 7/2008 |
| JP | 20090087067 A | 10/2010 |
| JP | 201015239 A | 8/2011 |
| WO | 2009045943 A2 | 4/2009 |

* cited by examiner

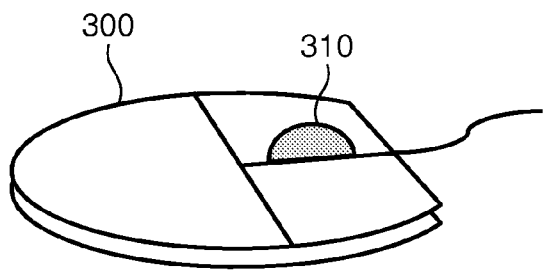
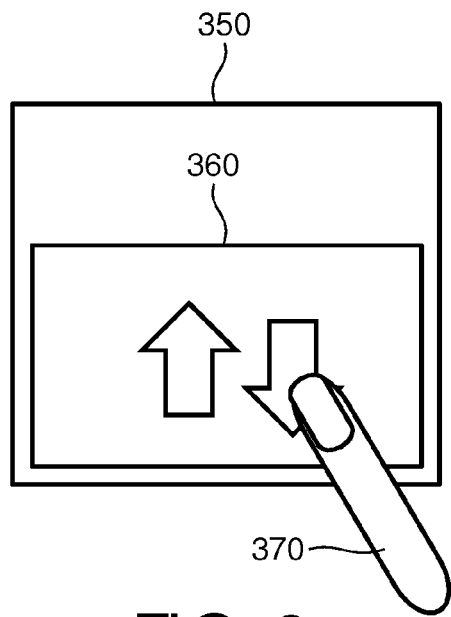
FIG. 5        FIG. 6
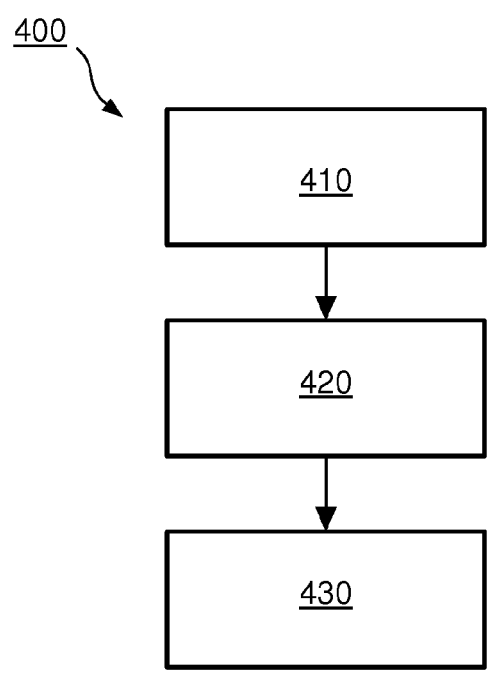
FIG. 7

MEDICAL IMAGE SYSTEM

FIELD OF THE INVENTION

The invention relates to a system for and a method of alerting a user to a region of interest within one image of a sequence of medical images from a patient.

BACKGROUND OF THE INVENTION

In the field of medical imaging, it is common to display a sequence of medical images from a patient. For example, Computed Tomography (CT) may provide a three-dimensional reconstruction of a human structure or tissue. For allowing a radiologist to navigate through the three-dimensional reconstruction, the three-dimensional reconstruction may be displayed as a sequence of two-dimensional cross-sections of the three-dimensional reconstruction, and the radiologist may be enabled to navigate through the sequence.

A particular image from the sequence of medical images may comprise a region that is of particular interest to the radiologist or other user. For example, Digital Breast Tomosynthesis (DBT) may provide a three-dimensional reconstruction of a patient's breast, and one of the cross-sections of the three-dimensional reconstruction may show a cluster of micro-calcifications which may be indicative of a pre-cancerous condition of the patient.

It is known to alert a user to a region of interest within a sequence of medical images from a patient. For example, US 2010/0086188 describes a system for facilitating the presentation of selected features in a set of reconstructed and/or projection breast images to a health professional. The features may be potential calcifications that meet certain criteria. The location of the features is obtained by a separate Computer-Aided Detection (CAD) step. Facilitating the presentation may comprise displaying selected breast images that comprise potential calcifications, and highlighting the calcifications in the images. Alternatively, potential calcifications may be outlined by a box, indicated by an arrow, or highlighted by a color and/or intensity change in the image in the vicinity of the potential calcifications.

A problem of the facilitated presentation of the region of interest according to US 2010/0086188 is that it is insufficiently suitable for alerting a user to a region of interest within one image of a sequence of medical images from a patient.

SUMMARY OF THE INVENTION

It would be advantageous to have an improved system or method for alerting a user to a region of interest within one image of a sequence of medical images from a patient.

To better address this concern, a first aspect of the invention provides a system for alerting a user to a region of interest within an image of interest, the image of interest being one of a sequence of medical images from a patient, the system being configured for sequentially displaying the sequence of medical images for enabling the user to navigate through the sequence of medical images, and the system comprising an input for receiving a sequence navigation command from the user for requesting the system to display images from the sequence of medical images as part of pixel data shown on a display, and a signal generator for providing a sensory signal to the user in separation from the pixel data and in dependence on a difference between a position of a currently displayed image of the sequence of medical images in the sequence and a position of the image of interest in the sequence.

The above system allows the user to relatively quickly browse through a relatively large amount of visual information from the sequence of medical images. At least one of the images from the sequence, the so-termed image of interest, comprises a region of interest. The region of interest is an identified portion of the image of interest. The location of the region of interest within the sequence, and consequently of the image of interest, is known to the system. The system may obtain the location from, for example, metadata accompanying the sequence, or from a separate region of interest detector within the system.

The system is arranged for allowing the user to request images from the sequence of medical images for navigating through the sequence. The images are shown on a display as part of all the pixel data being displayed on the display. The system further comprises a signal generator that is arranged for providing a sensory signal that is separated from, and thus not part of, the pixel data shown on the display. The signal generator provides the sensory signal in dependence on a difference in location within the sequence, of the image of interest and an image that is currently being displayed by the system. Hence, the system allows the user to navigate through the sequence while being alerted, separately from the pixel data shown on the display, to a relative position of an image that comprises the region of interest. Advantageously, the user may not need to be alert to the pixel data shown on the display to find the region of interest within the sequence of medical images.

The invention is partially based on the recognition that alerting the user to a region of interest within one image of a sequence of medical images from a patient using pixel data shown on the display is not ideal for the following reasons. A user may be visually focused on the sequence of medical images, and hence miss the pixel data associated with the alert. An alert shown on the display also adds additional visual information to the large amount of visual information already shown on the display. Disadvantageously, the user may be confused by being relatively overloaded with visual information on the display.

Alerting the user, using pixel data shown on the display, may also comprise discerning the region of interest from its surroundings. However, if the region of interest is insufficiently visually discerned, the user may not notice the region of interest. On the other hand, if the region of interest is visually too strongly discerned, the region of interest may be misinterpreted. For example, the region of interest may be discerned by an increase in intensity. Disadvantageously, this may lead to a misinterpretation of an increase in tissue density. The region of interest may also be discerned by a bounding box or similar graphical object. Disadvantageously, the bounding box may obscure adjacent regions relevant for interpreting the region of interest.

According to the invention, a sensory signal is provided separately from the pixel data on the display to indicate to the user the relative position of the image of interest. By providing such a sensory signal, the user is alerted independent of the pixel data shown on the display. Consequently, the sensory signal does not add to the visual information shown on the display. Advantageously, confusion of the user due to a relative overload of visual information on the display may be avoided. Furthermore, the user may be alerted without the system needing to discern the region of interest and thus without potentially increasing the risk of misinterpretation. Advantageously, the user may locate the image of interest and its region of interest relatively quickly and/or with little effort.

Optionally, the difference between the positions may be indicative of whether the currently displayed one of the sequence of medical images is the image of interest.

It may be desirable to provide the sensory signal when the currently displayed medical image is the image of interest. This provides an alert to the user that the region of interest is located in the currently displayed image. Similarly, it may also be desirable to provide the sensory signal when the currently displayed medical image is not the image of interest. This provides an alert to the user that the region of interest is located in another medical image. Advantageously, a user may know whether or not he needs to look for the region of interest in the currently displayed image. Advantageously, the user may locate the image of interest and its region of interest relatively quickly and/or with little effort.

The difference between the positions may be indicative of a distance or a navigation direction from the currently displayed one of the sequence of medical images to the image of interest in the sequence.

The distance and the navigation direction from the currently displayed medical image to the image of interest are both relevant for enabling the user to find the image of interest. For example, if the distance is provided to the user, he may navigate in a direction that decreases the distance. This allows the user to relatively quickly find the image of interest. Also, the navigation direction towards the image of interest allows the user to determine whether he is navigating towards or away from the image of interest. Hence, the sensory signal is provided to the user in dependence on the distance or the navigation direction. Advantageously, the user may locate the image of interest and its region of interest relatively quickly and/or with little effort.

The sensory signal may be a non-visual sensory signal.

By providing a non-visual sensory signal, the user is alerted using a different sensory modality. Consequently, the non-visual sensory signal does not add to the visual information provided by the sequence of medical images. Advantageously, a user may be more easily alerted to the region of interest when the user otherwise predominantly receives visual information. Also, confusion of the user due to a relative overload of visual information may be avoided. Advantageously, the user may locate the image of interest and its region of interest relatively quickly and/or with little effort.

The non-visual sensory signal may be an auditory and/or haptic signal.

An auditory signal and/or haptic signal are well-suited for alerting the user, as such signals differ relatively significantly from the visual information provided by the sequence of medical images. Advantageously, the user may be particularly alert for an auditory signal in a relatively quiet environment. Advantageously, the user may be particularly alert for a haptic signal in a relatively static environment.

The input may comprise a tactile input for receiving a tactile sequence navigation command from the user, and the sensory signal may be a haptic signal.

By providing the sensory signal as a haptic signal, the user is alerted to the region of interest, using the same sensory modality as the user is using to provide the sequence navigation command. Advantageously, the user may be already relatively alert to the particular sensory modality for correctly providing the desired input, and hence may be relatively easily alerted to the region of interest.

The input may further comprise the signal generator for providing the haptic signal to the user while receiving the tactile sequence navigation command from the user.

An input that also comprises the signal generator is particularly well-suited for alerting the user, using a haptic signal as the user is already in physical contact with the tactile input of the input for providing the tactile sequence navigation command. Advantageously, the user does not need to otherwise physically contact the system in order to receive the haptic signal.

The tactile input may be a scroll wheel for receiving the tactile sequence navigation command from the user by detecting a rotation of the scroll wheel by the user, and the signal generator may be configured for providing the haptic signal to the user by adjusting a rotational resistance of the scroll wheel.

A scroll wheel is well suited for providing the haptic signal to the user while receiving the tactile sequence navigation command from the user.

The tactile input may be a touch surface for receiving the tactile sequence navigation command from the user by detecting a touch to the touch surface from the user, and the signal generator may be configured for providing the haptic signal to the user by adjusting a vibration of the touch surface.

A touch surface is well suited for providing the haptic signal to the user while receiving the tactile sequence navigation command from the user.

The signal generator may be configured for providing the sensory signal in dependence on a medical image property of the region of interest, or in dependence on a second image of interest from the sequence of medical images, the second image of interest comprising a second region of interest.

The sensory signal may convey information other than only the relative position of the image of interest. In particular, a medical image property or a presence of a second region of interest in a second image of interest may be conveyed, for example, by suitably choosing the sensory signal. Advantageously, a single sensory signal may be used to provide an alert to the user with respect to the relative position of the image of interest and to convey additional information.

The medical image property may relate to a density value of the region of interest.

A workstation may comprise the system set forth.

An imaging apparatus may comprise the system set forth.

A method of alerting a user to a region of interest within an image of interest, the image of interest being one of a sequence of medical images from a patient, may comprise configuring a system for sequentially displaying the sequence of medical images for enabling the user to navigate through the sequence of medical images, and may comprise receiving a sequence navigation command from the user for requesting the system to display images from the sequence of medical images as part of pixel data shown on a display, and providing a sensory signal to the user in separation from the pixel data and in dependence on a difference between a position of a currently displayed image of the sequence of medical images in the sequence and a position of the image of interest in the sequence.

A computer program product may comprise instructions for causing a processor system to perform the method set forth.

The signal generator may be configured for providing the sensory signal to the user by adjusting an amplitude, frequency or pitch of a sensory carrier signal.

The sensory signal may be provided to the user by changing a characteristic of an existing sensory signal, i.e., a carrier signal. The characteristic may include an amplitude, frequency and/or pitch. For example, the sensory signal may be provided to the user by increasing an amplitude or frequency of the sensory carrier signal. The sensory signal may also be provided by successively changing the characteristic of the sensory carrier signal. This may allow additional information to be provided by the sensory signal. For example, the sensory carrier signal may be increased, decreased and then increased again in amplitude to indicate a particularly large region of interest, and may be only increased once to indicate a normally sized region of interest.

The system may further comprise a region of interest detector for detecting in the sequence of medical images the region of interest, based on some criteria for detecting a region of interest, to provide a position of the image of interest within the sequence of medical images. The criteria may be entered by the user as user input data. Alternatively, the detector may be adapted for using predetermined criteria, e.g. criteria for detecting a lung nodule or an occluded segment of the Left Anterior Descending (LAD) artery. The detection may be based, for example, on image segmentation such as adapting a deformable model of an object to the image or region growing, followed by an analysis of the grown region. A person skilled in the art will know many ways of implementing a region of interest detector.

The system is thus able to detect which one of the sequence of medical images comprises the region of interest. Hence, the system knows which one of the medical images is the image of interest, as the image of interest corresponds to the particular medical image that comprises the region of interest. Advantageously, the system does not need to obtain the location of the region of interest from an external source.

It will be appreciated by those skilled in the art that two or more of the above-mentioned embodiments, implementations, and/or aspects of the invention may be combined in any way deemed useful.

Modifications and variations of the image acquisition apparatus, the workstation, the method, and/or the computer program product, which correspond to the described modifications and variations of the system, can be carried out by a person skilled in the art on the basis of the present description.

A person skilled in the art will appreciate that the method may be applied to multi-dimensional image data, e.g. two-dimensional (2-D), three-dimensional (3-D) or four-dimensional (4-D) images, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

The invention is defined in the independent claims. Advantageous embodiments are defined in the dependent claims.

BRIEF DESCRIPTION OF THE DRAWINGS

These and other aspects of the invention are apparent from and will be elucidated with reference to the embodiments described hereinafter. In the drawings.

FIG. 5 shows an input device comprising a scroll wheel;

FIG. 6 shows an input device comprising a touch surface;

FIG. 7 shows a method of alerting a user to a region of interest within an image of interest.

DETAILED DESCRIPTION OF EMBODIMENTS

Figure 1:
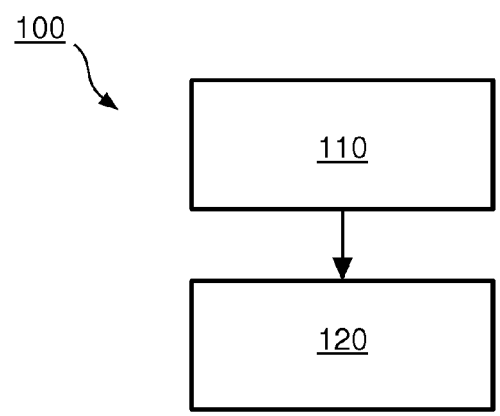
FIG. 1 shows a system for alerting a user to a region of interest within an image of interest.

FIG. 1 shows a system 100 for alerting a user to a region of interest within an image of interest, the image of interest being part of a sequence of medical images from a patient. The system 100 comprises an input 110 for receiving a sequence navigation command from the user for requesting the system to display images from the sequence of medical images. The system 100 further comprises a signal generator 120 for providing a sensory signal to the user in dependence on a difference between a position of a currently displayed image of the sequence of medical images in the sequence and a position of the image of interest in the sequence. Thus, the system 100 provides feedback to the user on a relative position of the image of interest within the sequence of medical images.

The input 110 may be a known user input device such as a keyboard, mouse or touch screen. Alternatively, the input 110 may be an electronic data input for receiving the sequence navigation command as electronic data from a user input device that is connected to the system 100. Furthermore, the signal generator 120 may be a physical signal generator such as a loudspeaker or a haptic signaling device that generates vibrations or electrical fields. Alternatively, the signal generator 120 may be an electronic signal generator for providing an electronic signal to a physical signal generator. The physical signal generator may then convert the electronic signal into its corresponding physical signal. The input 110 and/or the signal generator 120 may therefore be at least partially implemented as software for being executed on a processor. Alternatively, the input 110 and/or the signal generator 120 may be at least partially implemented as hardware.

The signal generator 120 shown in FIG. 1 is connected to the input 110. This may be for providing the sensory signal in direct dependence on the sequence navigation command from the user, e.g., for providing the sensory signal while the user provides the sequence navigation command. However, the signal generator 120 may not need to be connected to the input 110 within the system 100, as the sensory signal may not need to be provided in direct dependence on the sequence navigation command. The signal generator 120, however, may typically provide the sensory signal in indirect dependence on the sequence navigation command, as the sensory signal is provided in dependence on a position of the currently displayed image, and the user may determine the currently displayed image using the sequence navigation command.

The system 100 is configured for sequentially displaying the sequence of medical images for enabling the user to navigate through the sequence of medical images. For that purpose, the system 100 may further comprise (not shown): a processor, storage means, or a communications port. The processor may be arranged for executing instructions that are part of a medical image display program. The medical image display program may comprise at least a part of the input 110 and/or the signal generator 120. The storage means may comprise RAM, ROM, hard disk, removable media such as CD and DVD. The storage means may be used for storing the computer instructions and/or for storing medical image data. The communications port may be used for communications with another computer system, for example a server. The communications port may be arranged for being connected to a network such as a local area network, wide area network, and/or the Internet. The other computer system may be reached via the network, e.g., for retrieving medical image data.

Although not shown in FIG. 1, the system 100 may further comprise a display for displaying the images from the sequence of medical images. The display may be any suitable display, such as, e.g., a computer monitor or television. Alternatively, the system 100 may comprise a display output for providing a medical image to a display that is not part of the system 100. The display output may be a computer monitor output.

Figure 2:
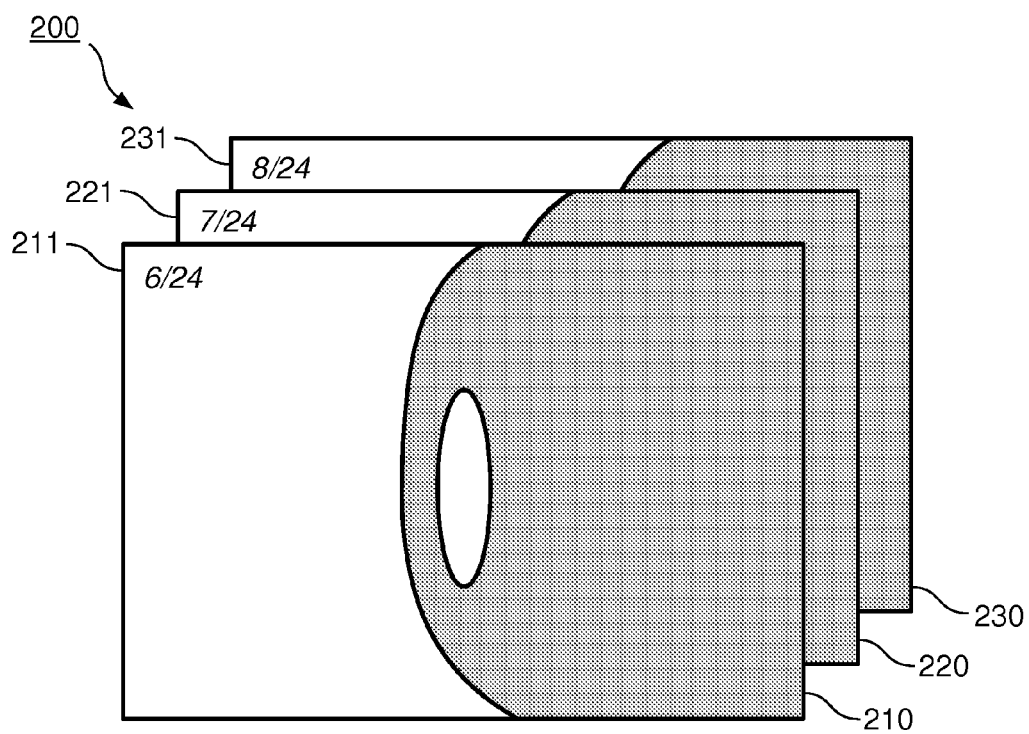
FIG. 2 shows a first one of a sequence of medical images being displayed.
Figure 3:
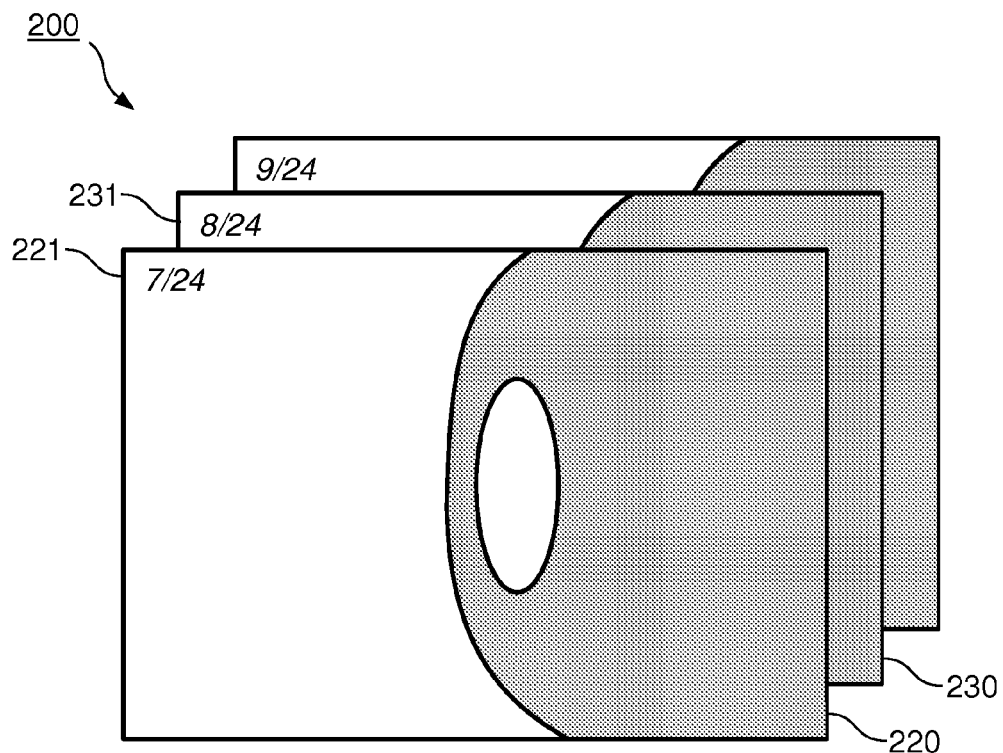
FIG. 3 shows a second one of the sequence of medical images being displayed, the second one being nearer to an image of interest in the sequence than the first one.
Figure 4:
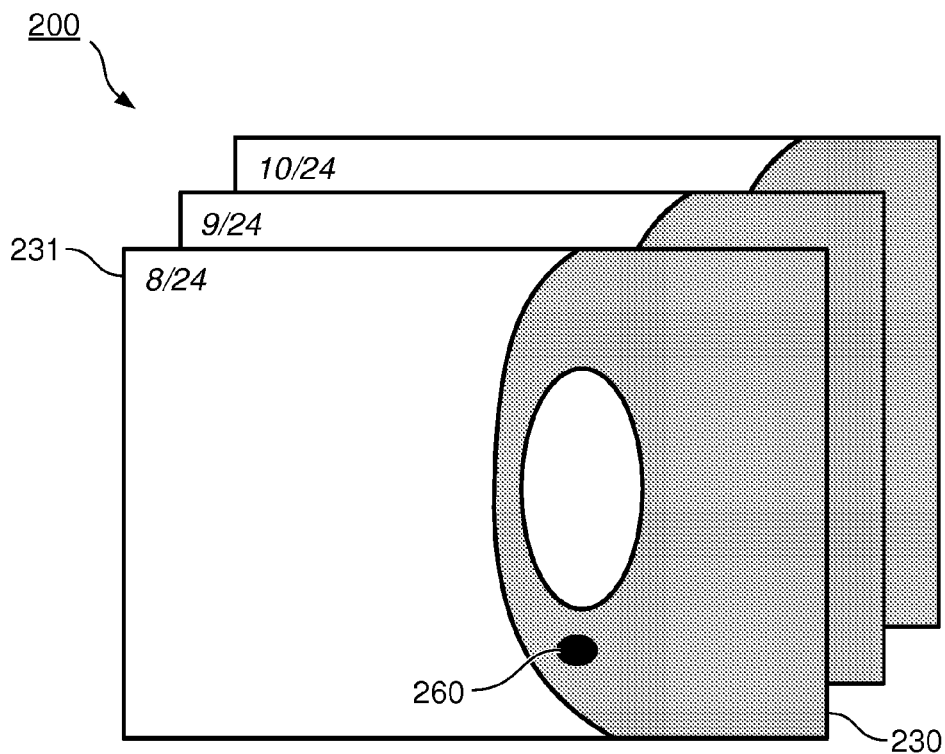
FIG. 4 shows a third one of the sequence of medical images being displayed, the third one being the image of interest and comprising a region of interest.

FIGS. 2-4 show consecutive phases of a possible operation of the system 100, and therefore may reflect what is displayed on a display means of the system 100 during operation. In FIG. 2, a first image 210 of the sequence 200 of medical images is displayed, i.e., a first image 210. The first image 210 is shown as an image on top of a stack of images that forms a representation of a part of the sequence 200. FIG. 2 thus also provides a partial view of a second 220 and third 230 one of the sequence 200, i.e., of a second image 220 and a third image 230, behind the first image 210. Of course, the system 200 may also display the sequence 200 of medical images in any other suitable manner. For example, it may be desirable to show only a single image at a time, i.e., the currently displayed image. This may allow the user to focus on the single image. Alternatively, the sequence 200 of medical images may be presented in a way similar to a filmstrip, for allowing a user to scroll through each image of the film strip, or as a volume rendering in which the first image is partially translucent for partially showing the second image and possibly further images.

The first image 210 has a position within the sequence 200. The position may be an image number if the sequence 200 comprises a limited number of medical images. The position may be shown to the user, for example by showing a position text 211 as shown in FIG. 2 or by showing a scroll bar that indicates the current position within a range representing the entire sequence 200. Since the first image 210 is the currently displayed image, the position text 211 reflects the currently displayed position within the sequence 200. However, the position may also be omitted from the image being displayed. FIG. 2 also shows the position text 221 of the second image 220 and the position text 231 of the third image 230.

FIG. 3 shows a result of the user providing a sequence navigation command. The system 100 has responded to the sequence navigation command by displaying the second image 220. This may be the result of the user issuing a 'next' or 'forward' sequence navigation command. It is shown in FIG. 4 that the next image within the sequence, i.e., the third image 230, is the image of interest, and thus comprises the region of interest 260. Therefore, the system 100 may be arranged for already providing a sensory signal that indicates that the currently displayed image 220 is near the image of interest 230. Thus, the user may be alerted to the nearby presence of the region of interest in the sequence 200.

The system 100 may determine that the image of interest 230 is near the currently displayed image 220 by comparing the positions between both images within the sequence 200. Comparing the positions may comprise calculating a difference between the positions. The system 100 knows the position of the image of interest 230 within the sequence, since the system knows the location of the region of interest 260. The system 100 may have obtained the location from an external source such as, e.g., metadata accompanying the sequence 200. Such metadata may comprise a spatial position and an image number. The image number may identify which one of the sequence of medical images comprises the region of interest. Hence, comparing the positions may comprise calculating the difference in image numbers. Alternatively, the system 100 may obtain the location from an internal source, e.g., a region of interest detector that is part of the system 100 for detecting the region of interest and the image of interest comprising the region of interest.

The system 100 may also provide a sensory signal that indicates the navigation direction from the currently displayed image 220 to the image of interest 230 within the sequence 200. Hence, the system 100 may provide a sensory signal indicating to the user that he may issue a 'next' or 'forward' command instead of, e.g., a 'previous' or 'backward'. FIG. 4 shows the result of the user issuing a further 'next' or 'forward' command, as the currently displayed image 230 shows the region of interest 260.

The system 100 may also provide the sensory signal to indicate a distance to the image of interest 230. For that purpose, the sensory signal may be provided by a sensory carrier signal having a particular characteristic. The carrier signal may be, e.g., an audio signal or a vibration of a particular amplitude or frequency. When a 'next' or 'forward' command is issued, causing the second image 220 to be presented, the carrier signal may be adjusted to indicate to the user that he has navigated nearer to the image of interest 230. For example, the carrier signal may be increased or decreased in amplitude and/or frequency. When a further 'next' or 'forward' sequence navigation command is issued and the third image, i.e., the image of interest 230, is presented, the carrier signal may be further adjusted to indicate to the user that the currently displayed image is the image of interest 230. The further adjustment may be a further increase or decrease of the amplitude and/or the frequency of the carrier signal.

It will be appreciated that instead of adjusting an amplitude, frequency or pitch of a sensory carrier signal, a new sensory signal may be provided that has an adjusted amplitude, frequency or pitch with respect to a previous sensory signal. It will be appreciated that a user's perception of the signal may be similar to, or the same as, adjusting an amplitude, frequency or pitch of a sensory carrier signal.

The system 100 may be arranged for providing a maximum or minimum amplitude of the sensory carrier signal when the currently displayed image is the image of interest 230. The system 100 may also be arranged for providing a maximum or minimum frequency of said carrier signal when the currently displayed image is the image of interest 230. Therefore, a user is provided with a sensory signal that is indicative of a distance from the currently displayed image to the image of interest 230. Similarly, the sensory signal may also be indicative of a navigation direction. For example, the system 100 may be arranged for providing a sensory signal having a different amplitude or frequency for either the navigation direction towards or away from the image of interest 230.

The sequence 200 of medical images is shown in FIGS. 2-4 as an explicit sequence of medical images, i.e., a stack of two-dimensional medical images. However, the sequence 200 may be implicitly formed by a direction of navigating through a three-dimensional medical image. For example, the system 100 may be arranged for allowing a user to navigate through a three-dimensional image, with the currently displayed image being a cross-section of the three-dimensional image along a particular plane, and the sequence 200 being implicitly formed by cross-sections of the three-dimensional image that are parallel to the particular plane. During operation, the particular plane may be rotated by the user. Hence, after rotation, the sequence of medical images 200 may be a new sequence of medical images implicitly formed by the new cross-sections that are parallel to the rotated plane. In this case, the difference in position may relate to a geometric distance within the three-dimensional image between the currently displayed cross-section and a cross-section of interest.

FIG. 5 shows a computer mouse 300 comprising a scroll wheel 310. The scroll wheel 310 is a mechanically rotatable device that may allow the user to navigate through the sequence 200. For example, rotating the scroll wheel 310 forward may issue a 'next' or 'forward' command, and rotating the scroll wheel 310 backward may issue a 'previous' or 'backward' command. Hence, the user may provide a tactile sequence navigation command to the system 100, as the scroll wheel 310 is operated by the user by touching and rotating the scroll wheel 310. The computer mouse 300 may also be arranged for providing the sensory signal to the user using the scroll wheel 310. Thus, the scroll wheel 310 may function as or be an embodiment of the signal generator 120. The sensory signal may be a rotational resistance that the user encounters when operating, i.e., rotating, the scroll wheel 310. Thus, the sensory signal is provided to the user at the same time as the user provides the sequence navigation command using the scroll wheel 310.

The rotational resistance may be indicative of a navigation direction. For example, the rotational resistance may be lower in a direction that is oriented towards the image of interest 230 in the sequence 200. For example, in an operating phase as depicted in FIG. 3, the rotational resistance for rotating the scroll wheel 310 backward may be higher than the rotational resistance for rotating the scroll wheel 310 forward. Consequently, the system may be arranged for adjusting the rotational resistance such that the user is able to find the image of interest 230 by scrolling, i.e., rotating, in a direction having the lowest rotational resistance. Alternatively, the rotational resistance may also be indicative of a distance. Alternatively, the computer mouse 300 or the scroll wheel 310 may provide as the sensory signal a vibration that is indicative of the distance or the navigation direction.

FIG. 6 shows an input device 350 comprising a touch surface 360. The touch surface 360 may be a top surface of a touch screen display. The input device 350 may be an embodiment of the input 110. The touch surface 360 may enable the user to provide the sequence navigation command by touching the touch surface. A portion of the touch surface may be associated with the 'next' or 'forward' command and another portion may be associated with the 'previous' or 'backward' command. The user may provide the associated commands by touching the respective portions of the touch surface 360 with his finger 370.

The input device 350 may be arranged for providing the sensory signal using the touch surface 360. Thus, the touch surface 360 may function as, or be an embodiment of, the signal generator 120. The sensory signal may be a vibration that the user encounters when operating, i.e., touching, the touch surface 360. Thus, the sensory signal may be provided at the same time as the sequence navigation command provided by the user. The vibration may be indicative of a navigation direction or of a distance. For example, in an operating phase as depicted in FIG. 3, the vibration that the user encounters when pressing the portion associated with the 'back' command may be stronger than the vibration encountered when pressing the portion associated with the 'forward' command. Alternatively, the vibration may be chosen such that the user, irrespective of which portion is touched, is provided with feedback indicating the navigation direction and/or the distance to the image of interest. Alternatively, the touch surface 360 may provide the sensory signal by any other suitable means, e.g., by generating an electrical field.

Although not shown, the input 110 may be arranged for receiving the sequence navigation command as a voice command. Therefore, the input 110 may comprise, or be connected to, a microphone. Also, the signal generator 120 may be arranged for providing the sensory signal as a synthesized or recorded voice signal. Therefore, the signal generator 120 may comprise, or be connected to, a loud speaker and/or voice synthesizer.

Although not shown, the signal generator 120 may comprise a light source that provides a visual sensory signal to the user in separation from the display. For example, the signal generator may comprise a Light Emitting Diode (LED) arranged adjacent to the display for providing the sensory signal as a light signal to the user. In a specific example, the LED is arranged on top of or below the display for providing a separate yet easily visible visual signal to the user. The signal generator may provide the light signal by, e.g., changing an intensity or color of the LED or by modulating a carrier LED light signal.

In general, the region of interest may indicate a particular medical aspect within the image of interest. The medical aspect may be a pathological aspect, such as a location of a calcification or a lesion. The medical aspect may also relate to a particular organ, and thus, the region of interest may indicate a location of, e.g., a heart or a liver. In particular, the region of interest may be indicated or marked by a Computer Aided Diagnosis (CAD) marker, e.g., for alerting the user to the presence of a calcification or a lesion. The CAD marker may be provided by metadata accompanying the sequence. The sequence may also comprise multiple regions of interest. Hence, the system may be arranged for alerting the user to each of the multiple regions of interest, and consequently, for providing the sensory signal in dependence on each of the images comprising a region of interest.

The sensory signal may be any sensory signal that may be provided separately from the pixel data of the display. In particular, the sensory data may be a non-visual sensory signal. The non-visual sensory signal may be an auditory, haptic, or any other suitable non-visual sensory signal. An auditory sensory signal may be a tone, a modulation of a tone, a synthesized voice, etc. A haptic sensory signal may be a vibration, a resistance, a pressure or an electronic stimulation applied to, e.g., a finger or hand of the user. It will be appreciated, however, that any other suitable non-visual sensory signals may be used as well.

The sensory signal may denote binary information, e.g., whether or not the region of interest is present within the currently displayed image. However, the sensory signal may also denote non-binary information, e.g., the distance to the image of interest, or a medical property of the region of interest within that image. The medical property may relate to, e.g., a density of the region of interest. The sensory signal may also comprise a code. For example, if the sensory signal is an auditory signal, a length of the auditory signal may be used to indicate a size or type of the region of interest. In a specific example, a short signal may indicate a single calcification, and a long signal may indicate a cluster of calcifications. Similarly, a letter of the Morse code alphabet may be used to indicate different types of medical anomalies. It will be appreciated that in general any coding technique known from the technical field of information theory may be used.

The sequence of medical images may also comprise an object or volume of interest, and a number of images from the sequence of medical images may comprise a respective number of regions of interest for indicating respective portions of the object or volume of interest. The sensory signal may be indicative of a medical property of the particular region of interest within the currently displayed image. The medical property may be, e.g., a density or mass. For example, a rotational resistance of the scroll wheel shown in FIG. 5 may be adjusted in dependence on the density of the currently shown portion of the object or volume of interest. Hence, the system 100 may signal to the user the density of the currently shown portion of the object or volume of interest through the scroll wheel.

The sequence of medical images may be obtained from Digital Breast Tomosynthesis (DBT) acquisition. Here, a breast of a patient is compressed parallel to a flat detector and irradiated from a limited angular range. A three-dimensional reconstruction of the breast may be obtained using limited-angle tomography reconstruction algorithms. Due to the limited angular range, the reconstructed volume admits an anisotropic resolution, i.e., the spatial resolution in planes parallel to the detector is significantly higher than in planes orthogonal to the detector. Therefore, the reconstructed data are shown as slice reconstructions with the possibility to scroll through the data along planes parallel to the detector. In standard mammography, a radiologist may make up a diagnosis based on one or two two-dimensional images. In the diagnosis of a sequence of DBT images, the radiologist may need to screen a series of DBT images and therefore may need more time. Furthermore, tiny structures such as clusters of micro-calcifications may be missed by the radiologist in the large amount of data from the series of DBT images. Hence, the system 100 may address or solve the need for more time and/or the tiny structures being missed.

FIG. 7 shows a method 400 of alerting a user to a region of interest within an image of interest, the image of interest being one of a sequence of medical images from a patient, the method comprising configuring 410 a system for sequentially displaying the sequence of medical images for enabling the user to navigate through the sequence of medical images, and the method comprising receiving 420 a sequence navigation command from the user for requesting the system to display images from the sequence of medical images as part of pixel data shown on a display, and providing 430 a sensory signal to the user in separation from the pixel data and in dependence on a difference between a position of a currently displayed image of the sequence of medical images and a position of the image of interest in the sequence.

It will be appreciated that the invention also applies to computer programs, particularly computer programs on or in a carrier, adapted to put the invention into practice. The program may be in the form of a source code, an object code, a code intermediate source and object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or to be used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for alerting a user to a region of interest within an image of interest, the image of interest being one of a sequence of medical images from a patient, the system being configured for sequentially displaying the sequence of medical images for enabling the user to navigate through the sequence of medical images, and the system comprising:

an input for receiving a sequence navigation command from the user for requesting the system to display images from the sequence of medical images as part of pixel data shown on a display, and includes one or more processors; and a signal generator for providing a non-visual sensory signal to the user in separation from the pixel data and which changes in dependence on a difference between a position of a currently displayed image of the sequence of medical images in the sequence and a position of the image of interest in the sequence, and includes the one or more processors.

2. The system according to claim 1, wherein the changes in the non-visual sensory signal includes an indication of whether the currently displayed image of the sequence of medical images is the image of interest.

3. The system according to claim 1, wherein changes in the non-visual sensory signal includes an indication of the difference of a distance or a navigation direction from the currently displayed image of the sequence of medical images to the image of interest in the sequence.

4. The system according to claim 1, wherein the non-visual sensory signal is at least one of an auditory signal or a haptic signal.

5. The system according to claim 1, further comprising:
a region of interest detector for detecting the region of interest in the sequence of medical images, based on criteria for detecting said region of interest, to provide the position of the image of interest within the sequence of medical images.

6. The system according to claim 1, wherein the input comprises:
a tactile input for receiving a tactile sequence navigation command from the user; and wherein the non-visual sensory signal is a haptic signal.

7. The system according to claim 6, wherein the input further comprises:
the signal generator for providing the haptic signal to the user while receiving the tactile sequence navigation command from the user.

8. The system according to claim 7, wherein the tactile input is a scroll wheel for receiving the tactile sequence navigation command from the user by detecting a rotation of the scroll wheel by the user; and wherein the signal generator is configured for indicating the changes of providing the haptic signal to the user by adjusting a rotational resistance of the scroll wheel.

9. The system according to claim 7, wherein the tactile input is a touch surface for receiving the tactile sequence navigation command from the user by detecting a touch to the touch surface from the user; and wherein the signal generator is configured for indicating the changes of providing the haptic signal to the user by adjusting a vibration of the touch surface.

10. The system according to claim 1, wherein the signal generator is configured for providing the non-visual sensory signal in dependence on a medical image property of the region of interest, or in dependence on a second image of interest from the sequence of medical images, the second image of interest comprising a second region of interest.

11. The system according to claim 10, wherein the medical image property relates to a density value of the region of interest.

12. A workstation comprising the system according to claim 1.

13. An imaging apparatus comprising the system according to claim 1.

14. A method of alerting a user to a region of interest within an image of interest, the image of interest being one of a sequence of medical images from a patient, the method comprising configuring a system for sequentially displaying the sequence of medical images for enabling the user to navigate through the sequence of medical images, and the method comprising:
receiving a sequence navigation command from the user for requesting the system to display images from the sequence of medical images as part of pixel data shown on a display; and
providing a non-visual sensory signal to the user in separation from the pixel data and which changes in dependence on a difference between a position of a currently displayed image of the sequence of medical images in the sequence and a position of the image of interest in the sequence.

15. A non-transitory storage media including a computer program product comprising instructions for causing a processor system to perform the method according to claim 14.

16. A system for alerting a user to a region of interest within an image of interest, the image of interest being one of a sequence of medical images from a patient, the system being configured for sequentially displaying the sequence of medical images for enabling the user to navigate through the sequence of medical images, and the system comprising:
an input for receiving a sequence navigation command from the user for requesting the system to display images from the sequence of medical images as part of pixel data shown on a display, and includes one or more processors; and
a signal generator for providing a non-visual sensory signal which changes to the user at least according to a difference between a position of a currently displayed image of the sequence of medical images in the sequence and a position of the image of interest in the sequence, and includes the one or more processors.

17. The system according to claim 16, wherein the non-visual sensory signal is an auditory signal.

18. The system according to claim 16, wherein the input comprises:
a tactile input for receiving a tactile sequence navigation command from the user; and
wherein the non-visual sensory signal is a haptic signal.

19. The system according to claim 18, wherein the tactile input is a touch surface for receiving the tactile sequence navigation command from the user by detecting a touch to the touch surface from the user; and
wherein the signal generator is configured for indicating the changes of providing the haptic signal to the user by adjusting a vibration of the touch surface.

20. A workstation comprising the system according to claim 16.

* * * * *